United States Patent [19]

Bruzzese et al.

[11] Patent Number: 5,189,149

[45] Date of Patent: Feb. 23, 1993

[54] METHOD FOR THE PRODUCTION OF COMPLEXES OF LONG CHAIN POLYUNSATURATED FATTY ACIDS AND THEIR DERIVATIVES, WITH CYCLODEXTRINS, AND THE RESULTING COMPLEXES

[75] Inventors: Tiberio Bruzzese; Giovanni Mozzi, both of Milan, Italy

[73] Assignee: Staroil Limited, Road Town, British Virgin Isls.

[21] Appl. No.: 736,565

[22] Filed: Jul. 26, 1991

[30] Foreign Application Priority Data

Aug. 9, 1990 [IT] Italy ................................ 21257 A/90

[51] Int. Cl.$^5$ ........................ C08B 37/16; A61K 47/40
[52] U.S. Cl. ........................................ 514/58; 536/103
[58] Field of Search ..................... 536/1.1; 514/23, 54, 514/58, 529, 546, 578, 724, 739

[56] References Cited

U.S. PATENT DOCUMENTS 4,438,106 3/1984 Wagu et al. .......................... 536/103
4,834,985 5/1989 Elger et al. .......................... 536/103

FOREIGN PATENT DOCUMENTS 2550445 2/1985 France .
2596617 10/1987 France .

*Primary Examiner*—Nathan M. Nutter
*Attorney, Agent, or Firm*—Oblon, Spivak, McClelland, Maier & Neustadt

[57] ABSTRACT

A method for the production of a complex formed by a long chain polyunsaturated fatty acid, a salt of it, alkyl ester $C_1$–$C_3$ or glyceride, or a mixture thereof, with a cyclodextrin, and the resulting complex.

19 Claims, No Drawings

METHOD FOR THE PRODUCTION OF COMPLEXES OF LONG CHAIN POLYUNSATURATED FATTY ACIDS AND THEIR DERIVATIVES, WITH CYCLODEXTRINS, AND THE RESULTING COMPLEXES

BACKGROUND OF THE INVENTION

Field of the Invention

The present invention concerns a method of producing complexes of long chain polyunsaturated fatty acids, their salts and esters inclusive of fish and vegetable oil glycerides, with cyclodextrins ($\alpha$-, $\beta$- and $\gamma$-cyclodextrin and hydroxypropyl-$\beta$-cyclodextrin), and the resulting complexes.

The dietetic and pharmaceutical use of fish oils and of polyunsaturated fatty acids in the form of glycerides is expanding due to their fat lowering ability (Y. Tamura et al., Prog. Lipid. Res., 25, 461, 1986; C. Von Schacky, Ann. Intern. Med., 107, 890, 1987), their platelet anticoagulant properties (C.R.M. Hay et al., Lancet, ii, 1269, 1982), and usefulness in the prevention and treatment of the most important cardiovascular diseases. Additionally, pressing evidence regarding other therapeutic uses for these materials is arising: in the treatment of psoriasis, rheumatoid arthritis (J.M. Kremer et al., Ann. Intern. Med., 106, 497, 1987; R.T. Sperling et al., Arth. Rheum., 30, 988, 1987), polyposis of the colon , arterial hypertension (K.M. Bonaa et al., N. Engl. J. Med., 322, 795, 1990; M.R. Knapp et al., N. Engl. J. Med., 320, 1037, 1989) and in the therapy of cancer.

Unfortunately, fish oils, some vegetable oils, and the polyunsaturated fatty acids that make them up, as well as certain derivatives of these materials, exhibit characteristics which markedly limit their use: they are liquid at room temperature, unctuous, and have an unpleasant taste and odour. They are easily oxidized in air owing to the large number of carbon-carbon double bonds in their molecules, and the consequent deterioration over time of organoleptic characteristics and the potential formation of epoxy groups are considered to provide toxic effects.

These characteristics markedly curtail the dietetic and pharmaceutical use of these products. For instance, dosage forms such as tablets are precluded as are hard gelatin capsules, syrups, drinking vials, and water-dispersible granules in single dose sachets.

In practice, the sole pharmaceutical form of these materials that is used is soft gelatin capsules, normally of considerable size owing to the rather high dosage typically necessary (up to several grams daily). This extra large size makes the use of the capsules by the elderly, who are the principal users owing to the pathologies mentioned above, quite difficult. These patients would have no difficulty if they were to take e.g., syrups or water dispersible granules.

In an attempt to overcome these disadvantages, U.S. Pat. No. 4 438 106 describes inclusion compounds of eicosapentaenoic acid (EPA) and docosahexaenoic acid (DHA), their alkaline salts and alkyl esters, in cyclodextrin, obtained by a complexation reaction occurring in the presence of large quantities of a polar organic solvent and through boiling. In the resulting complexes, the quantity of oleaginous substance is never more than 15% by weight, even under the best conditions. A 15% by weight concentration of active substance requires that frequent daily doses be administered in order to attain the pharmacologically active quantity of active ingredient; moreover, oversize dosage units must be prepared to ensure such quantities, not to mention the excessive use of the complexant cyclodextrin which is inactive per se but has a negative impact on the cost of the finished product. Moreover, the use of large quantities of organic solvents negatively influences the production costs and presents rather considerable risks to the operator (fire, explosion, intoxication by inhalation) and to the user (unavoidable traces of solvents in the finished product).

SUMMARY OF THE INVENTION

It has now surprisingly been discovered that a process requiring n organic solvents permits the production of complexes of long chain polyunsaturated fatty acids, their salts and esters, inclusive of fish and vegetable oil glycerides, with cyclodextrins ($\alpha$-, $\beta$- and $\gamma$-cyclodextrin and hydroxypropyl-$\beta$-cyclodextrin) having a content by weight of oleaginous substance which is significantly higher than the limits known in the art as mentioned above, with the consequent avoidance of the above described disadvantages.

More particularly, the method of the invention comprises: dissolution of cyclodextrin in simple, preferably distilled, water, introduction of the active oleaginous substance in the resulting solution so as to thereby obtain a heterogenus mixture, submission of the mixture to stirring for from about 1 to about 24 hours at a temperature of between 0° and 100° C., preferably room temperature, from which the desired complex precipitates in a solid, crystalline form; the complex is recovered by filtration and thereafter washed and dried. The washing of the invention complex is carried out with either water or with an organic solvent such as methanol, ethanol, etc., or a mixture of these organic solvents and water. Drying may be done in oven at a moderate temperature.

The resulting products are characterized by the fact that the concentration of oleaginous substance present in the complex is higher than 18% by weight, preferably from about 20% to about 50% by weight.

Complexation is performed with various types of fish oils, vegetable oils and long chain polyunsaturated fatty acids, their salts and alkyl and glycerol esters, with cyclodextrins present in varying degrees of polymerization and substitution. By way of example, natural fish oils can be used (mackerel, trout, herring, sardines, tuna fish, salmon , cod, etc.) or purified fish oils, or even oils concentrated by known techniques in glycerides containing polyunsaturated acids having high molecular weight. Starting from the acids themselves, analogous complexes were prepared in a free or variously salified form, or from the corresponding $C_1$–$C_3$ esters (preferably from ethyl esters), or from the relative glycerides obtained through synthesis.

Preference is given to the use of $\omega$-3 polyunsaturated fatty acids since they are considered to be the pharmacologically most active constituents of fish oils, and the $\omega$-6 fatty acids, typical of some vegetable oils. Of the $\omega$-3 polyunsaturated fatty acids, the long chain ones ($C_{20}$–$C_{22}$), more precisely cis-5,8,11,14,17-eicosapentaenoic acid (EPA) and cis-4,7,10,13,16,19-docosahexaenoic acid (DHA) and their derivatives, in particular the ethylesters, are considered most interesting. Of the $\omega$-6 fatty acids, preference is given to $\gamma$-linolenic acid ($C_{18}$) and its derivatives.

All of the above mentioned compounds can be present in the oils used in the complexation, either alone, as a single component, or as a mixture of them in a varying ratio.

The cyclodextrins that can be used in complexation may be either α-, β- or γ-cyclodextrin, characterized by 6, 7 or 8 D-glucopyranoside units forming a cyclic cavity. Hydroxypropyl-β-cyclodextrin can also be used; it is derived from β-cyclodextrin through total or partial replacement of the hydroxyls of the ring-forming glucoside units with an —O—CH₂—CHOH—CH₃ radical or one of its polymers

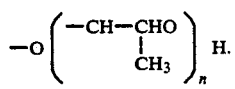

Unlike the pure oleaginous substances used in preparing these complexes, the new complexes themselves are gliding, not unctuous, nearly odourless and tasteless powders that can therefore be used to prepare a variety of compositions with various pharmaceutical forms such as tablets, hard gelatin capsules, syrups, drinking vials, water dispersible granules in sachets, etc. Furthermore, they maintain their satisfactory initial organoleptic and chemical characteristics over time since the complex stability is better than the starting oils stability. In this context the term 'complexes' means inclusion compounds of long chain polyunsaturated substances enclosed in the hydrophobic cavities of the cyclodextrins.

EXAMPLES

The following examples are solely given to better illustrate the invention, but in no way are they to be intended as limiting the scopes of the invention itself.

Methods

The oil present in the complex was determined by taking a U.V. absorption spectrum at 195 to 300 nm of an ethanol solution of the complex and then comparing the maximum absorbance with that obtained from an analogous standard solution.

The gas-chromatographic determination (G.C.) of the oil present in the complex was performed on a chloroform extract of it under the following operative conditions:

| | |
|---|---|
| internal standard: | 0.003% methyl palmitate |
| column: | SBT$^{TB}$-1, 15 m, 0.25 mm int. dia., 0.25μ thickness |
| injection port: | PTV |
| splitting: | 1:70 |
| column temp. | programmed at from 160 to 240° C. |
| carrier gas: | helium |
| adjuvant gas: | nitrogen |
| detector: | F.I.D. |

The yields were obtained by calculating the percent ratio between product obtained and sum of oil plus starting cyclodextrin.

The cyclodextrins used contained varying quantities of water (up to 12%). In the following examples the percent assay values of the cyclodextrins used are shown in brackets.

EXAMPLE 1

Dissolve 9.5 g of β-cyclodextrin (assay value about 88% calculated on the substance as such) in 100 ml of distilled water at 60° C. At a temperature of 55° C. and while stirring add 6.5 g of oleaginous substance containing DHA ethylester (assay value ≧ 80%). Sonicate, allow to stand for 1 h at 45° C. then homogenize with ULTRA-TURRAX. Filter, wash the solid residue with 20 ml of methanol and dry it in an oven at 45° C. The product obtained contains 27% of oil (UV assay value calculated on substance as such) equivalent to a molar ratio to β-cyclodextrin of about 1.25. : 1.

EXAMPLE 2

Dissolve 18.1 g of β-cyclodextrin (assay value about 88% calculated on the substance as such) in 500 ml of distilled water at 40°–45° C. Cool to room temperature and while stirring add 5 g of oleaginous substance containing DHA ethylester (assay value ≧ 80%). Cool immediately to 2° C. and maintain under stirring at this temperature for 7 h. Filter, wash with about 50 ml of distilled water and dry in oven at 45° C. The product obtained with a yield of about 85%, contains 23.7% of oil (G.C. assay value on the dey product) equivalent to a molar ratio to β-cyclodextrin of about 1:1.

EXAMPLE 3

Dissolve 18.1 g of β-cyclodextrin (assay value about 88% calculated on the substance as such) in 500 ml of distilled water at 40°–45° C. Cool to room temperature and add 10 g of oleaginous substance containing DHA ethylester (assay value ≧ 80%) Agitate on shaker for 22 h at 26° C. Filter, wash with about 50 ml of distilled water and dry in an oven at 45° C. The product, obtained with a yield of about 93%, contains 38.5% of oil (G.C. assay value on the dry product) equivalent to a molar ratio to P-cyclodextrin of about 2 : 1.

EXAMPLE 4

Dissolve 38 g of β-cyclodextrin (assay value about 88% calculated on the substance as such) in 1 litre of distilled water at 40°–45° C. Cool to room temperature and while stirring add 20 g of oleaginous substance containing EPA and DHA ethylesters (combined assay value >80%). Maintain under stirring at room temperature for 7 h. Filter, wash with about 100 ml of distilled water and dry in an oven at 45° C. The product, obtained with a yield of about 90%, contains 36.6% of oil (G.C. assay value on the dry product), equivalent to a molar ratio to β-cyclodextrin of about 2:1.

EXAMPLE 5

Dissolve 19 g of β-cyclodextrin (assay value about 88% calculated on the substance as such) in 500 ml of distilled water at 40°–45° C. Cool to room temperature and while stirring add 17.3 g of oleaginous substance containing EPA and DHA ethylesters (combined assay value ≧ 80%). Maintain under stirring at room temperature for 7 h. Filter, wash with about 50 ml of distilled water and dry in an oven at 45° C. The product, obtained with a yield of about 80%, contains 44.4% of oil (G.C. assay value on the dry product), equivalent to a molar ratio to β-cyclodextrin of about 3:1.

EXAMPLE 6

Dissolve 3.2 g of α-cyclodextrin (assay value about 90% calculated on the substance as such) in 20 ml of distilled water and while stirring add 1 g of oleaginous substance containing EPA and DHA ethylesters (combined assay value≧80%). Maintain under stirring at room temperature for 5 h. Filter, wash with about 10 ml of distilled water and dry in an oven at 45° C. The product, obtained with a yield of about 96%, contains 26.3% of oil (G.C. assay value on the dry product), equivalent to a molar ratio to α-cyclodextrin of about 1:1.

EXAMPLE 7

Dissolve 4.2 g of γ-cyclodextrin (assay value about 90% calculated on the substance as such) in 20 ml of distilled water and while stirring add 1 g of oleaginous substance containing EPA and DHA ethylesters (combined assay value≧80%). Maintain under stirring at room temperature for 5 h. Filter, wash with about 10 ml of distilled water and dry in an oven at 45° C. The product, obtained with a yield of about 96%, contains 20.3% of oil (G.C. assay value on the dry product), equivalent to a molar ratio to 7-cyclodextrin of about 1:1.

EXAMPLE 8

Dissolve 3.9 g of β-cyclodextrin (assay value about 88% calculated on the substance as such) in 100 mi of distilled water at 40°-45° C. Cool to room temperature and while stirring add 1 g of oleaginous substance containing EPA and DHA triglyceride esters (combined assay value>50%). Maintain under stirring at room temperature for 4.5 h. Filter, wash with about 20 ml of distilled water and dry in an oven at 45° C. The product, obtained with a yield of about 80%, contains 22.2% of oil (U.V. assay value on the dry product), equivalent to a molar ratio of the triglyceride acid radical to β-cyclodextrin of about 1:1.

EXAMPLE 9

Dissolve 3.4 g of β-cyclodextrin (assay value about 88% calculated on the substance as such) in 50 ml of distilled water at 40°–45° C. Cool to room temperature and dissolve 1 g of DHA sodium salt. Maintain under stirring at room temperature for 3 h and evaporate the solution to dryness under reduced pressure then wash the residue with 5 ml of distilled water, filter and dry in an oven at 45° C. The product obtained contains 20.6% of DHA sodium salt (U.V. assay value on the dry product), equivalent to a molar ratio to β-cyclodextrin of about 1:1.25.

EXAMPLE 10

Dissolve 4.2 g of β-cyclodextrin (assay value about 88% calculated on the substance as such) in 100ml of distilled water at 40°–45° C. Cool to room temperature and while stirring add 1 g of an oleaginous substance containing EPA acid (assay value≧80%). Maintain under stirring at room temperature for 5.5 h. Filter, wash with about 20 ml of distilled water and dry in an oven at 45° C. The product obtained contains 19.6% of oil (U.V. assay value on the dry product), equivalent to a molar ratio to cyclodextrin of about 1:1.

EXAMPLE 11

Dissolve 4.6 g of β-cyclodextrin (assay value about 88% calculated on the substance as such) in 100 ml of distilled water at 45°-50° C. Cool to room temperature and while stirring add 1 h of an oleaginous substance containing γ-linolenic acid (assay value≧85%). Maintain under stirring at room temperature for 4.5 h. Filter, wash with about 20 ml of distilled water and dry in an oven at 45° C. The product, obtained with a yield of about 80%, contains 19.5% of oil (U.V. assay value on the dry product), equivalent to a molar ratio to β-cyclodextrin of about 1:1.

EXAMPLE 12

Dissolve 3.9 g of β-cyclodextrin (assay value about 88% calculated on the substance as such) in 100 ml of distilled water at 40°-45° C. Cool to room temperature and add 2 g of oleaginous substance containing EPA ethylester (assay value≧80%). Agitate on a shaker for 22 h at 26° C. Filter, wash with about 20 ml of distilled water and dry in an oven at 45° C. The product, obtained with a yield of about 90%, contains 5.7% of oil (U.V. assay value on the dry product), equivalent to a molar ratio to β-cyclodextrin of about 2:1.

EXAMPLE 13

Dissolve 4.2 g of β-cyclodextrin (assay value about 88% calculated on the substance as such) in 100 ml of distilled water at 45°-50° C. Cool to room temperature and while stirring add 1 g of oleaginous substance containing γ-linolenic acid ethylester (assay value≧80%). Maintain under stirring at room temperature for 4.5 h. Filter, wash with about 20 ml of distilled water and dry in an oven at 45° C. The product, obtained with a yield of about 85%, contains 21.4% of oil (U.V. assay value on the dry product), equivalent to a molar ratio to 7-cyclodextrin of about 1:1.

Obviously, numerous modifications and variations of the present invention are possible in light of the above teachings. It is therefore to be understood that within the scope of the appended claims, the invention may be practiced otherwise than as specifically described herein.

We claim:

1. A complex consisting of an oleaginous substance and a cyclodextrin, and oleaginous substance being selected from the group consisting of long chain polyunsaturated fatty acids, salts, of long chain polyunsaturated fatty acids, $C_1$-$C_3$ alkyl or glycerol esters of long chain polyunsaturated fatty acids and mixtures thereof, characterized in that the active oleaginous substance is present in the complex in a concentration higher than 18% by weight.

2. A complex in accordance with claim 1 in which the active oleaginous substance is present in a concentration of from about 20% to about 50% by weight.

3. A complex in accordance with claims 1 or 2 in which the long chain polyunsaturated fatty acids belong to the ω-3 or ω-6 series.

4. A complex in accordance with claims 1 or 2 in which the long chain polyunsaturated fatty acids have a chain of 18-22 carbon atoms.

5. A complex in accordance with claim 3 in which the ω-3 series acids are selected from the group consisting of eicosapentaenoic acid and docosahexaenoic acid.

6. A complex in accordance with claim 3 in which the ω-6 series acids are γ-linolenic acid 7. A complex in accordance with claims 1 or 2 in which the alkyl esters of the long chain polyunsaturated fatty acids are ethylesters.

8. A complex in accordance with claims 1 or 2 in which the cyclodextrin is selected from the group consisting of α-, β-and γ-cyclodextrin and hydroxypropyl-β-cyclodextrin.

9. A complex in accordance with claim 2 consisting essentially of eicosapentaenoic acid ethylester and β-cyclodextrin.

10. A complex in accordance with claim 2 consisting essentially of docosahexaenoic acid ethylester and β-cyclodextrin.

11. A complex in accordance with claim 2 consisting essentially of eicosapentaenoic acid ethylester, docosahexaenoic acid ethylester and β-cyclodextrin.

12. A pharmaceutical formulation containing the complex of claims 1 or 2, further comprising a pharmaceutically acceptable excipient.

13. A method for preparing a dietetic or therapeutic formulation comprising adding the complex of claims 7 or 8 to a dietetic or therapeutic formulation which lacks the complex of claims 1 or 2.

14. A method for producing a complex containing from greater than 18% by weight to about 50% by weight of an oleaginous substance and a cyclodextrin, said oleaginous substance being selected from the group consisting of long chain polyunsaturated fatty acids, salts of long chain polyunsaturated fatty acids, $C_1$-$C_3$ alkyl or glycerol esters of long chain polyunsaturated fatty acids and mixtures thereof, consisting of dissolving cyclodextrin in water, adding the active oleaginous substance to the resulting solution so as to form a heterogeneous mixture, submitting the heterogeneous mixture to stirring for a period of 1 to 24 hours at a temperature of between 0° C. and 100° C., recovering the desired complex which precipitates in the form of a crystalline solid by filtration, and washing and drying the crystalline solid.

15. A method in accordance with claim 14 in which cyclodextrin is dissolved in distilled water.

16. A method in accordance with claims 14 or 15 in which the temperature at which the heterogeneous mixture is submitted to stirring is room temperature.

17. A method in accordance with claim 14 wherein cyclodextrin is selected from the group consisting of α-, β-, γ-cyclodextrin and hydroxypropyl-β-cyclodextrin.

18. A method in accordance with claim 14 wherein the fatty acids are selected from the group consisting of eicosapentaenoic acid, docosahexaaenoic acid and γ-linolenic acid.

19. A method in accordance with the claim 14 wherein washing of the filtered complex is performed with water or with an organic solvent or with a mixture thereof.

* * * * *